United States Patent [19]
Hopkins

[11] Patent Number: 4,711,131
[45] Date of Patent: Dec. 8, 1987

[54] METHOD AND APPARATUS FOR DETERMINING CRACK INITIATION AND PROPAGATION IN METALS

[75] Inventor: Daniel N. Hopkins, Dallas, Tex.

[73] Assignee: Mobil Oil Corporation, New York, N.Y.

[21] Appl. No.: 815,847

[22] Filed: Jan. 3, 1986

[51] Int. Cl.$^4$ ............................................. G01N 19/00
[52] U.S. Cl. .................................... 73/799; 73/865.6
[58] Field of Search ................. 73/799, 865.6, 826; 436/6; 374/46

[56] References Cited

U.S. PATENT DOCUMENTS

| | | | |
|---|---|---|---|
| 2,986,928 | 6/1961 | White | 73/799 X |
| 4,075,886 | 2/1978 | Barker | 73/826 X |
| 4,152,941 | 5/1979 | Abou-Sayed et al. | 73/799 |
| 4,179,940 | 12/1979 | Oertle et al. | 73/808 |

FOREIGN PATENT DOCUMENTS

| | | | |
|---|---|---|---|
| 926561 | 5/1982 | U.S.S.R. | 73/799 |
| 1065722 | 1/1984 | U.S.S.R. | 73/799 |

Primary Examiner—Jerry W. Myracle
Attorney, Agent, or Firm—Alexander J. McKillop; Michael G. Gilman; Charles A. Malone

[57] ABSTRACT

A method and apparatus for determining crack initiation and propagation in metals subjected to environmental conditions encountered in drilling deep wells wherein strain sensors are used to measure crack initiation and propagation so that a prediction can be made about the life expectancy of the metal in actual operating conditions.

51 Claims, 6 Drawing Figures

METHOD AND APPARATUS FOR DETERMINING CRACK INITIATION AND PROPAGATION IN METALS

FIELD OF THE INVENTION

This invention is directed to a method and apparatus for detecting and monitoring crack initiation and propagation in metals.

BACKGROUND OF THE INVENTION

Because of the growing scarcity of hydrocarbonaceous fluids, there is a continuous need to find additional hydrocarbonaceous reserves. In order to find these hydrocarbonaceous reserves, it is necessary to explore deeper and into more hostile environments to obtain hydrocarbonaceous fluids. Metals used in oil country tubular goods must therefore encounter more harsher environments than previously known. Thus, oil country tubular goods and other metals similarly used in the exploration and production of hydrocarbonaceous fluids must endure greater pressures, hotter temperatures, greater hanging stresses, and harsher chemical environments than previously enountered.

Much interest has therefore been directed into ways for determining how metals will react in these harsher environments. As is generally known, similar type metals, which bear the same type designation, often vary considerably in their behavior in actual operating conditions. There has been much conjecture as to why these variations occur, particularly when the metals are obtained from the same manufacturer. To remove these vexations, others have taught methods for determining the fatigue and relaxation potentials of metals under stress. One such method is disclosed by Oertle et al. in U.S. Pat. No. 4,179,940 issued Dec. 25, 1979. Via this method crack initiation in metallic structure members subjected to cyclic loading was predicated by sensing metallurgical changes taking place as a result of cyclic loading. Fatigue loading produced a cycle comprising a condition described as fatigue relaxation followed by fatigue intensification. By monitoring this cycle, measured strain for a known applied load would increase or decrease. By monitoring the change in strain load, crack initiation could be predicated as fatigue relaxation became fatigue intensification. In a preferred embodiment, a strain gauge was mounted beneath a patch, which patch excluded ambient atmosphere during monitoring of the structural members.

Therefore, what is needed is a method to predict how a metal will behave in a hostile environment which environment includes exposure to heated chemicals, higher pressures, and physical stresses greater than heretofore encountered.

SUMMARY OF THE INVENTION

This invention is directed to a method for predicting crack initiation and subsequent crack propagation in metals under operating conditions where strain sensors are utilized. In the practice of this invention, the operating conditions to which the metal will be exposed are determined. Afterwards, a specimen of said metal has attached thereto at least two of said strain sensors where said sensors have affixed thereto a means for measuring data. This data is obtained electrically from the crack initiation and subsequent propagation via said sensors. Thereafter, the specimen is placed into a means for simulating the operating conditions. Subsequently, data obtained from said simulated operating conditions under which the crack is initiated and propagated in said specimen is measured. From this data, a practitioner of this invention is able to predict crack initiation and propagation in a pipe or other member made of the metal under actual operating conditions. Via this prediction, a member containing said metal can be replaced as required.

It is therefore an object of this invention to evaluate the behavior of metals and metallic alloys in a substantially deep subterranean chemical environment, particularly a hydrogen sulfide environment.

Another object of this invention is to measure crack initiation and propation in metals and metallic alloys in a simulated environment which includes prssures, temperatures, and chemical conditions which would be encountered at extreme depths while producing and exploring for hydrocarbonaceous fluids.

A yet further objective of this invention is to identify metals and metallic alloys which are suitable for use in hostile environments encountered in the deep exploration and production of hydrocarbonaceous fluids.

It is a still further object of this invention to use these metals and metallic alloys which have been identified as suited for use in deep exploration and production of hydrocarbonaceous fluids to lessen the frequency of interruptions in said production and exploration operations due to materials failures.

It is a still yet further object of this invention to provide an efficient, and less costly method for testing metals under the conditions encountered during actual operations, particularly where high pressures are encountered.

DESCRIPTION OF THE PREFERRED EMBODIMENTS

In the practice of this invention, a specimen is obtained of the metal to be tested and utilized in actual operating conditions. The sample or specimen may comprise a double cantilever beam (DCB). A compact tensile specimen can be used. A description of a double cantilever beam and one test procedure therefor under ambient temperature and conditions, is discussed in an article by R. B. Hedley entitled *Evaluation of Sulfide Corrosion Cracking Resistance in Low Alloy Steels*. This article was contained in a paper which was presented during the Corrosion/75 Seminar given April, 1975 in Toronto, Ontario, Canada. This article is hereby incorporated by reference in its entirety.

Metals and metallic alloys which can be tested in the practice of this invention include members selected from the group consisting of carbon steel, chromium alloys, corrosion resistant alloys, precipitation hardenable alloys, duplex alloys, austenitic stainless steel, nickel-based alloys, and cobalt-based alloys. Of course, any other similar metals or metallic alloys can be tested according to this method as will be readily apparent to those skilled in the art.

In order to determined how metals will react in a deep drilling environment encountered in the exploration and production of hydrocarbonaceous fluids, it is desired to have a procedure which will simulate the operating conditions encountered therein. When exploring at depths of about 10,000 feet to about 20,000 feet, pressures up to about 15,000 psig may be encountered. Also, hydrogen sulfide may be encountered in amounted up to about 10% by volume and carbon dioxide may be encounered in amounts up to about 50% by volume. Temperatures encountered at these depths may range from about 200° F. to about 500° F.

Figure 1:
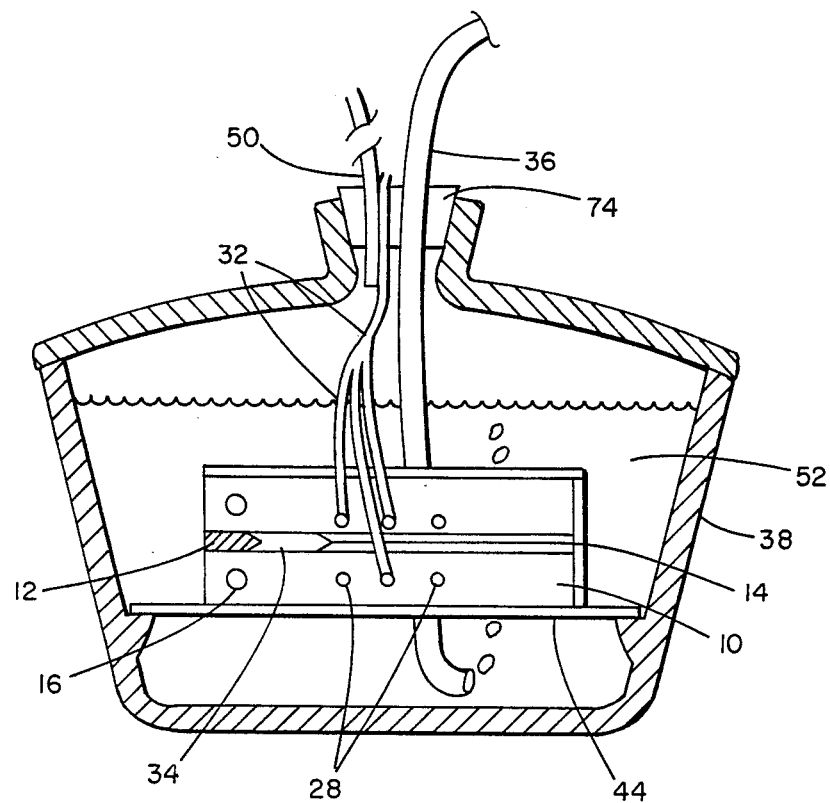
FIG. 1 is a sectional view of a test chamber with a wedge loaded double cantilever beam of a metallic or metallic alloy specimen which has attached thereto strain sensors.

One embodiment for simulating less severe operating conditions is shown in FIG. 1. Referring to FIG. 1, a double cantilever beam (DCB) 10 has affixed thereto at least one pair of strain sensors 28. DCB 10 is positioned on support 44. Although one pair of strain sensors 28 can be utilized, it is preferred to use at least two pairs of said strain sensors. Affixed to these strain sensors are wires 32 which pass through an opening in stopper 74 and afterwards are connected to the data measuring equipment (not shown). This equipment measures and records electrical impules emitted from strain sensors 32. Afterwards, a wedge 12 is driven into the opening or slot 34 of DCB 10 thereby loading the opposing arms of said DCB which loading simulates stresses which are expected to be encountered under actual operating conditions.

The specimen is thereafter placed into a test chamber 38. Chamber 38 typically contains a mixture 52 of distilled water, 5% by weight NaCl and 0.5% by weight glacial acetic acid. Dissolved oxygen is removed from the mixture by vigorously bubbling nitrogen through gas entry tube 36 for about thirty minutes. Thereafter, hydrogen sulfide is quickly bubbled through tube 36 for about 15 minutes to initially saturate the solution, and finally, hydrogen sulfide is slowly bubbled to ensure that the solution remains saturated. Excess gas is vented from chamber 38 via line 50 thereby maintaining a substantially atmospheric pressure within said chamber. Conditions in chamber 38 are maintained at ambient temperatures. As mentioned above, wires 32 are connected to the data measuring equipment (not shown) and the data is gathered as the test progresses. The duration of a test is usually 14 days but tests can continue for up to 6 months. As is known to those skilled in the art, test duration will depend upon the metals and simulated conditions.

As the test progresses, electrical voltage measurements are obtained as the crack initiates and propagates in the DCB. These electrical measurements can be made and recorded on commercially available equipment. Crack propagation is monitored continuously. A measurement is taken at the time when the crack is first initiated in the DCB. The extent to which the crack propagates in the DCB and the rate of such propagation is a measure of how well the metal from which the DCB specimen was obtained will withstand operating conditions actually encountered in deep subterranean formations.

Strain sensors 28 which can be used in the practice of this invention may comprise strain gauges. Strain gauges sufficient for this purpose are disclosed in U.S. Pat. No. 4,179,940 which issued to Oertle et al. and which is hereby incorporated by reference.

When a crack is first initiated, an electrical change takes place in the metal adjacent to a pair of strain sensors 28. This electrical change is measured and recorded in volts. As the crack propagates between another pair of strain sensors, another electrical change is detected and recorded. Knowing the time and distance covered by the crack enables one skilled in the art to determine how fast the crack is propagating. The electrical changes can be recorded and computations made to determine how fast the crack is propagating. The rate of crack propagation will enable one skilled in the art to forecast how well the metal will withstand actual use conditions in the environment which has been simulated.

To duplicate environmental conditions encountered by metals in deep wells, a DCB 10 is placed within an autoclave 26 which has a means for automatically loading DCB 10 which loading simulates stress conditions expected to be enountered under actual operating conditions. This embodiment is shown in FIG. 2.

Figure 2:
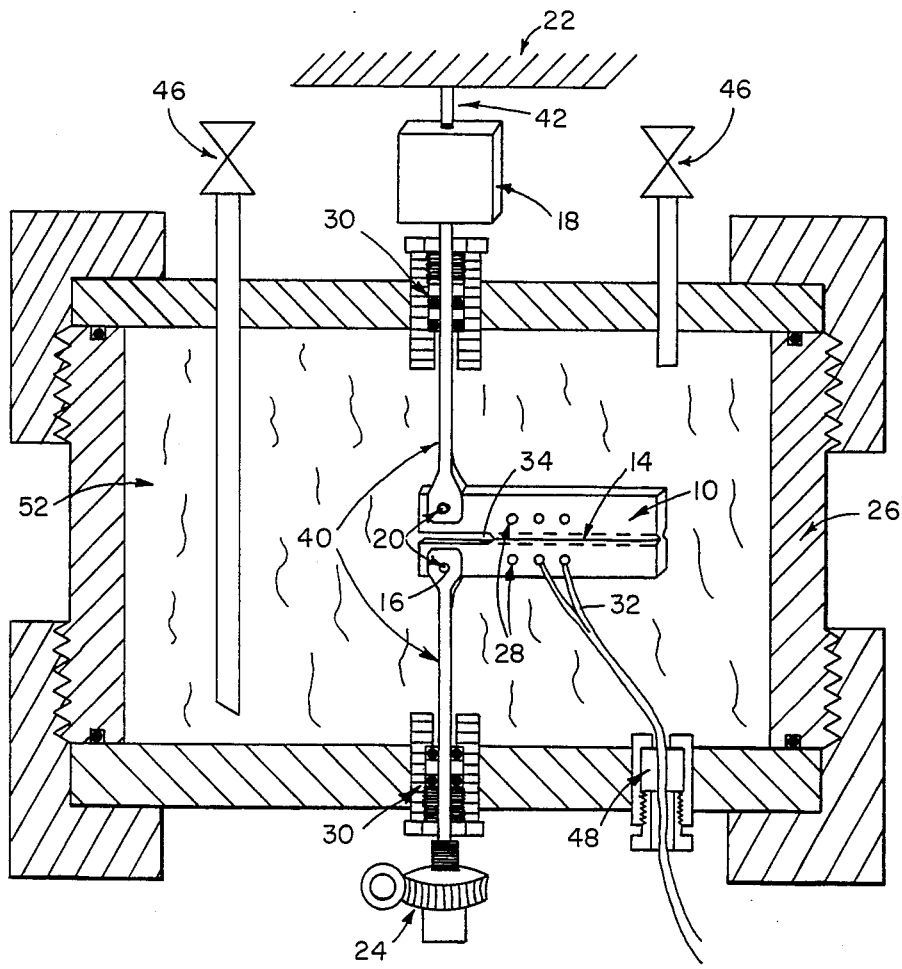
FIG. 2 is a side plan view of a double cantilever beam of a metallic or metallic alloy specimen in an autoclave which beam has affixed thereto an adjustable loading means and strain sensors.

FIG. 2 shows another embodiment of the invention where slow dynamic stress is applied directly to a DCB within autoclave 26 that contains a simulated downhole environment. Strain gauges 28 and the wires 32 are coated to protect them from the environment. Wires 32 are then fed through a suitable pressure seal 48. Liquid plastics that harden when exposed to ultraviolet light can be used to isolate the strain gauges from the environment. Isolation of the strain gauges in this manner allows said gauges to withstand exposure times similar to those expected to be encountered in a down-hole environment. Dentists use similar plastic material to seal pits and fissures in teeth. Sliding pressure seals 30 prevent the gas and liquid 52 in the autoclave from leaking out around the loading connectors 40. The appropriate liquid and gas mixture is added to the autoclave using the valve and tubing assemblies 46. These mixtures will be in proportion to these liquids and gases expected to be encountered by the metal in actual use.

Figures 3, 4:
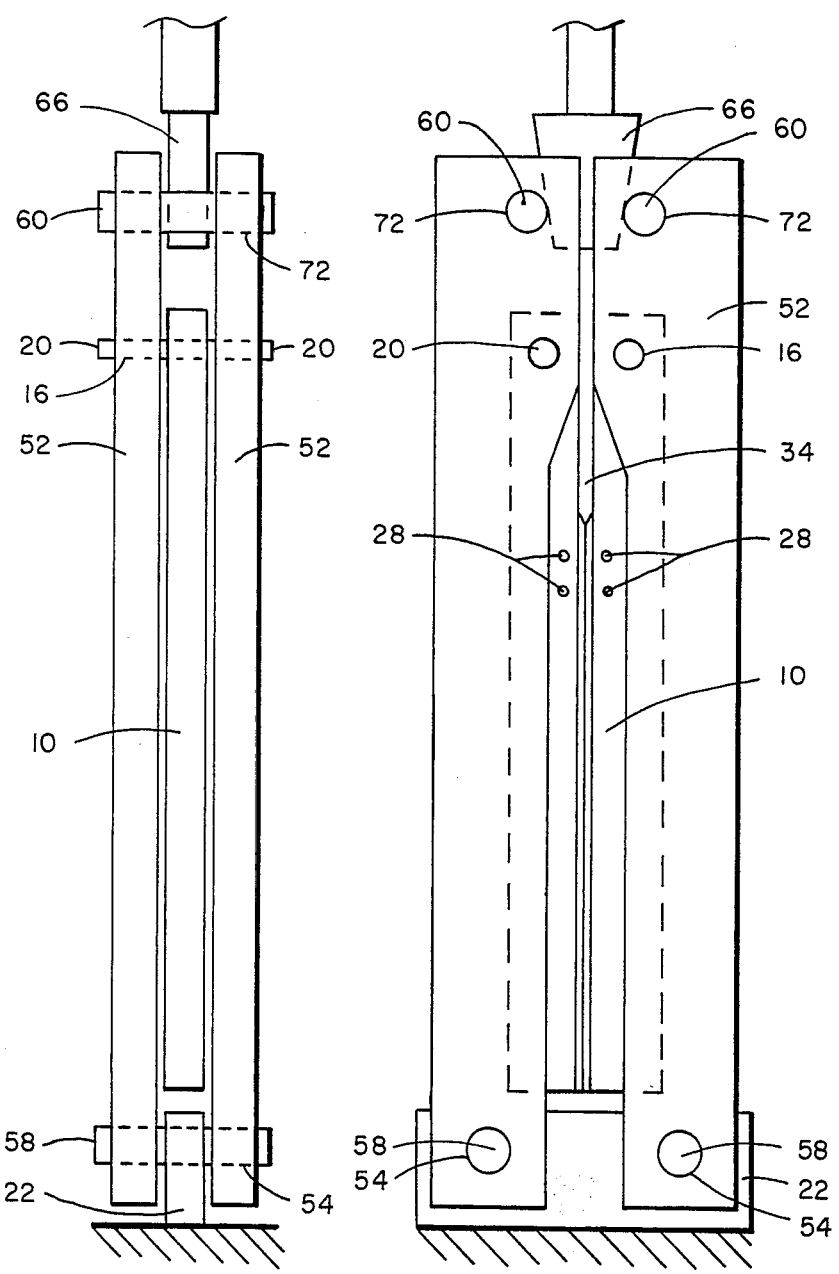
FIG. 3 is a frontal representation of a double cantilever beam confined within a means for holding and applying stress to said double cantilever beam.
FIG. 4 is a side view representation of a double cantilever beam depicting the interconnecting relationship between the means for holding and applying pressure and a double cantilever beam.

Referring to FIG. 2, a DCB 10 has affixed there to at least one pair of strain sensors 28 in the vicinity of notch 14. Although one pair of sensors can be utilized, as before stated, it is preferred to use two or more sets of said strain sensors. Affixed to these strain sensors are wires 32 which are connected to the measuring equipment (not shown). Stress may be applied to the DCB 10 by loading the connectors 40 that are attached to pins 20 placed into each of the holes 16 in the DCB (FIG. 3). Stress applied to DCB 10 from gearing 24 can be measured with a load cell 18 that is mechanically attached to a stationary member 22 by second connector 42. Load cells suitable for the purpose of this invention are obtainable from Alpha-Tron Corporation located in North Andover, Mass.

As shown in FIG. 2, a DCB 10 is placed into autoclave 26. In order to withstand pressures of up to about 20,000 psig and temperatures of about 400° to about 600° F., generally about 500° F., which is sufficient to duplicate conditions normally encountered in the deepest commercial hydrocarbonaceous wells, the autoclave should be lined with annealed Hastelloy C-276® alloy. This allow should be used to protect the wetted autoclave surfaces from corrosion. Similarly, load connectors 40, pins 20, and similar parts exposed within autoclave 26, can be made of Hastelloy C-276 or another similar material. Hastelloy C-276 is a product of Cabot Corp. of Kokomo, Ind. Seals 30 are provided in the side of autoclave 26 which seals are sufficient to withstand pressures up to about 20,000 psig. Through these seals proceeds a connector 40 which connects with the pin 20 in hole 16 of DCB 10. The opposite end of connector 40 is attached to a load cell 18 which can be used to measure the load on the DCB 10. Load cell 18 is affixed to a stationary member 22 by connector 42. One end of connector 40 is connected to a gearing arrangement 24 which can be used to apply and vary loading on DCB 10. Wires leading from strain sensors 28 are connected to data measuring equipment (not shown).

Sufficient water is placed in autoclave 26 to cover DCB 10. Generally, the water will comprise about 70% by volume of the capacity of autoclave 26. Hydrogen sulfide is injected into the autoclave 26 to pressures up to and including the hydrogen sulfide saturation pressure.

In order to more accurately simulate the conditions encountered in deep drilling of wells, carbon dioxide in an amount of about 1 to about 50 volume percent is also placed into autoclave 26. A substantially non-corrosive gas, a member of which is selected from the group comprising nitrogen, methane, and other light hydrocarbonacous gases, is injected into autoclave 26 to ultimately reproduce the downhole equilibrium pressure desired to be simulated. Thereafter, the autoclave is closed so that the gases cannot escape. After closing the autoclave 26, it is pressured up to about 2,000 to about 20,000 psig, preferably about 14,000 psig. The temperatures is then raised to about 200° to about 700° F., preferably about 500° F. These conditions are sufficient to simulate a depth of about 5,000 feet to about 25,000 feet, preferably about 20,000 feet in a hydrocarbonaceous well. The autoclave is equipped with a means for automatically adjusting temperature and pressure. This equipment is available from commercial sources known to those skilled in the art.

Electrical measurements are then taken, as mentioned above, as the test progresses to determine when a crack is initiated and also the rate at which the crack is propagated in DCB 10. After about 30 days, the measurements are stopped, the data collected, and the results are interpreted. Based on the rate of crack propagation after initiation thereof, a prediction can be made as to the ability of the metal in actual operating conditions to withstand the conditions which will be encountered when drilling into deep formations for hydrocarbonaceous fluids.

In the practice of this invention, the hydrogen sulfide partial pressure can be from about 10 to about 1,000 psig depending upon the hydrogen sulfide pressures anticipated to be encountered when drilling into a deep formation. The carbon dioxide partial pressure can be from about 0.5 to about 500 psig partial pressure to similate the actual conditions which are anticipated to be encountered in the formation when drilling to extended depths. Although the autoclave can withstand a pressure of about 20,000 psig, it is preferred to operate the autoclave at a pressure of from about 2,000 to about 17,000 psig for safety reasons preferably about 14,000 psig.

In another embodiment as shown in enlarged FIGS. 3 and 4, an indirect method is depicted for applying slow dynamic stress to a vertically positioned double cantilever beam as opposed to the direct method of applying stress as depicted in FIGS. 1 and 2. Per this embodiment, referring to FIG. 3, a DCB 10 is placed in a vertical position within a means for holding said DCB 52 and applying stress thereto. With CDB 10 vertically positioned via pins 20 into holes 16 said DCB is maintained in an upright vertical position by stationary member 22. By maintaining DCB 10 in a vertical position, available corrosion resistant oil country tubular goods can be used to fashion autoclave 26. Thus, an inexpensive autoclave can be fashioned. Positioning DCB 10 in a vertical position within autoclave 26 allows for use of a smaller diameter autoclave, which can withstand much higher pressures for a given wall thickness. Stationary pins 58 are positioned through said stationary member 22 and the front and rear holding means 52 via openings 54. Wedge pins 60 are positioned through front and rear holding means 52 via pins 72 for receipt of a wedge 66 which will apply stress to said pins 60 through said holding means 52.

Figure 5:
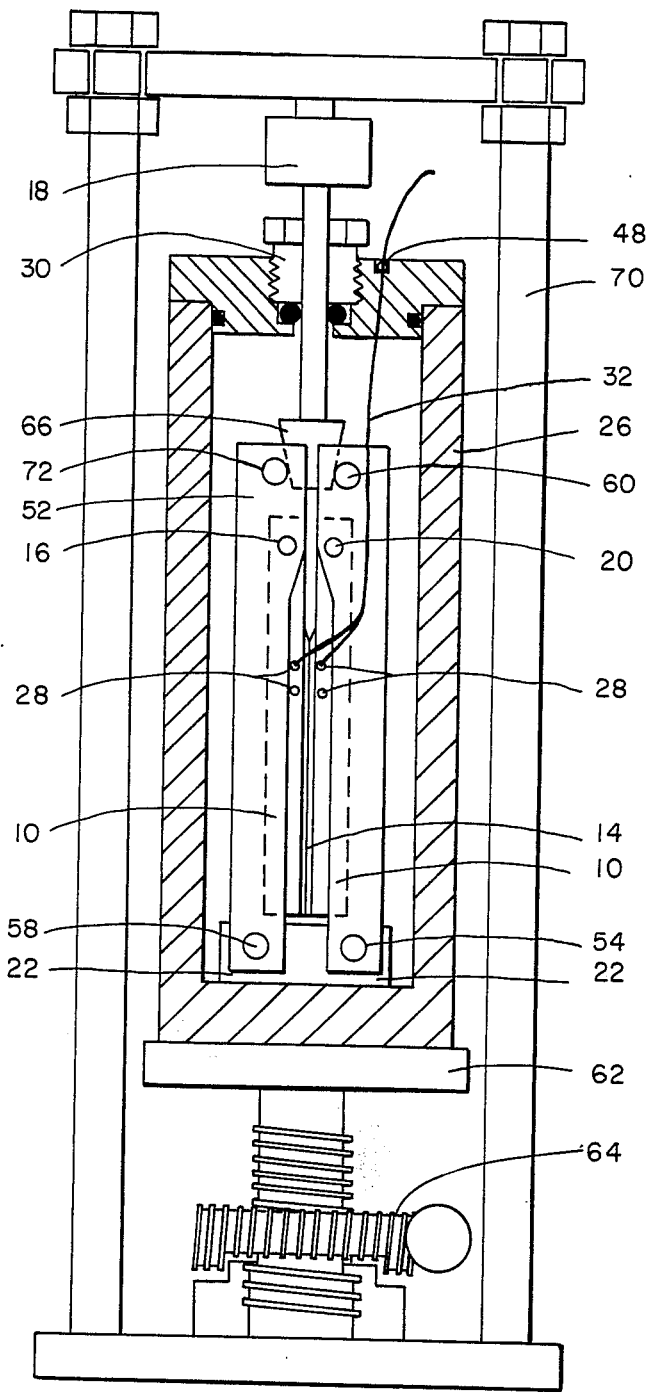
FIG. 5 is a frontal view of a vertically positioned DCB contained within an autoclave which is subjected to indirect stress via a mechanical screw means.

Hydraulic and mechanical means can be used to position the moveable support 62. In FIG. 5, a mechanical screw means 64 is used to position moveable support 62 causing said stress to be exerted on load cell 18 which is transmitted through wedge pins 60 which causes stress to be exerted against holding means 52 which stress is transmitted through pins 20 to DCB 10. Strain sensors 28 are connected to wires 32 and electrical measurements made pursuant to the discussion regarding the embodiment in FIG. 1 supra. The instant embodiment which utilizes an indirect stress means can be used in lieu of the solid driven wedge (direct dynamic stress embodiments in FIG. 1) to determine crack initiation and propagation as discussed in FIG. 1 supra. The less severe operating conditions and equipment discussed in conjunction with FIG. 1 can be simulated similarly in the indirect stress embodiment.

By extending the screw means 64, as shown in FIG. 5, slow dynamic stress can be indirectly applied to moveable support means 62 and the remainder of the test procedure followed by utilizing the embodiments discussed in conjunction with FIGS. 3 and 4. Load frame 70 stabilizes and restrains movement of autoclave 26 when gearing and screw means 64 is used to apply slow dynamic stress to DCB 10 via said mechanical means. Because of the vertical positioning of the DCB within said holding means 52, a substantially smaller autoclave can be used. Since the diameter of the autoclave is substantially reduced, substantially thicker walls can be produced economically.

Upon placement of a gearing means 64, as discussed in the embodiment concerning FIG. 2, slow dynamic stress can be produced in an autoclave upon connection of the worm and gear means with screw means 64 as shown in FIG. 5. Other appropriate equipment and conditions as discussed in regards to the embodiment contained in FIG. 2, can be used to simulate severe conditions encountered in deep wells. As mentioned above, a substantially smaller diameter autoclave can be used when the DCB is vertically positioned and indirectly stressed. As is anticipated, the inside diameter of the autoclave maybe about 4–6 inches.

Figure 6:
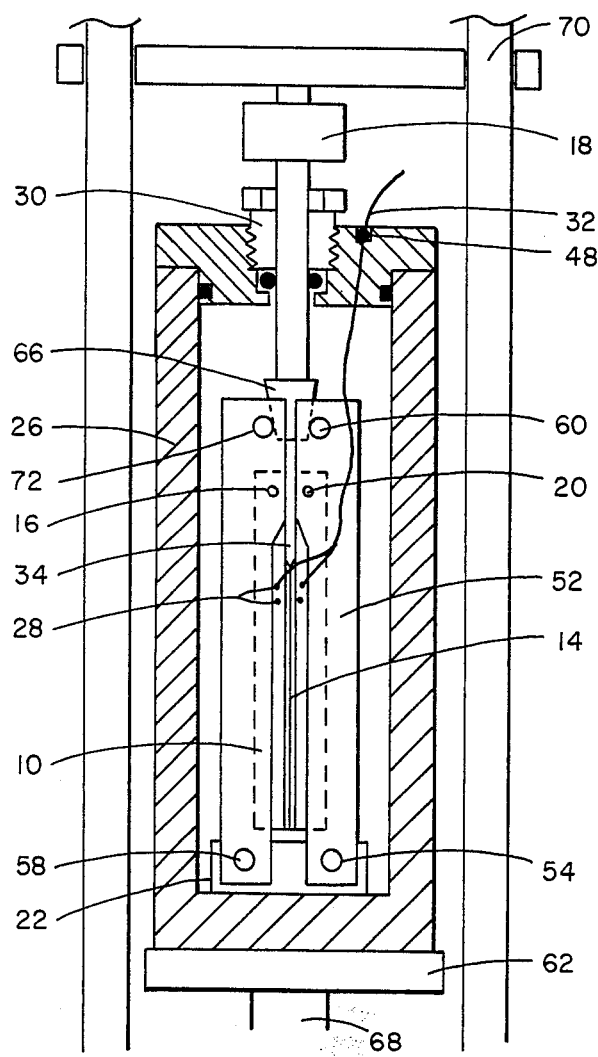
FIG. 6 is a cross sectional view of a vertically positioned and indirectly stressed DCB contained within an autoclave which is subjected to stress via a hydraulic means.

FIG. 6 shows another embodiment where a hydraulic ram means 68 is used to exert dynamic stress indirectly upon DCB 10 via moveable member 62. Load frame 70 stabilizes autoclave 26 as hydraulic pressure is applied thereto.

Normalization of these forces is expected to result in standardization and uniformity of interpretation of lab results involving past and presently accepted DCB testing protocols.

Upon following the teachings of this method, one skilled in the art will have a method and apparatus which will cancel forces except those normal to a DCB which will result in substantially pure mode one stress at the base of the slot in the DCB. Mode one stress is described in a book entitled *Application of Fracture Mechanics for Selection of Metallic Structural Materials* edited by James E. Campbell et al. which was published by The American Society for Metals, Metals Park, Ohio 44073. This publication was copyrighted in 1982. Other "fracture mechanics" books should contain similar descriptions, as is known by those skilled in the art.

Although the present invention has been described with preferred embodiments, it is to be understood that modifications and variations may be resorted to without departing from the spirit and scope of this invention, as those skilled in the art will readily understand. Such modifications and variations are considered to be within the purview and scope of the appended claims.

What is claimed is:

1. An apparatus with an enclosed environment conducive to crack initiation and propagation comprising:
    (a) means for supporting a metal specimen in said enclosed environment;
    (b) a specimen of a generally rectangular planar and cross sectional configuration having two longitudinal arms with a space therebetween for a substantially short distance terminating in oppositely disposed longitudinal grooves for the remainder of the distance therebetween which grooves define a narrowed longitudinal section;
    (c) means for applying a force, while said specimen is in said enclosed environment by a rod means interconnected to each of said arms in combination with said enclosed environment, sufficient to initiate and propagate a longitudinal crack in said longitudinal section; and
    (d) a means for detecting strain via strain sensors and a mean for measuring said detection results from said crack initiation and propagation in said specimen which enables the prediction of the metal behavior under actual conditions of use.

2. The apparatus as recited in claim 1 where said specimen is contained in a means for exposing said specimen to high pressures and high temperatures in combination with gases generally encountered in deep wells.

3. The apparatus as recited in claim 1 wherein said specimen is contained within an autoclave where conditions encountered in deep wells are simulated.

4. The apparatus as recited in claim 1 where said rod means comprises two separate rods interconnected into holes in each of said arms which are thereafter connected to a gearing means and a load cell for monitoring the load applied to said arms.

5. The apparatus as recited in claim 1 where said means for applying force comprises an enclosure around said specimen having at least two pins which pass through said enclosure and said specimen whereby said force is indirectly transferred to said specimen.

6. The apparatus as recited in claim 1 where the means for detecting said strain comprises at least one pair of strain sensors.

7. The apparatus as recited in claim 1 where said means for detecting said strain comprises at least one pair of strain gauges.

8. The apparatus as recited in claim 1 where said specimen is a member selected from the group consisting of carbon steel, chromium alloys, corrosion resistant alloys, precipitation hardenable alloys, duplex alloys, austenitic stainless steel, nickel-based alloys, and cobalt-based alloys.

9. The apparatus as recited in claim 1 where said specimen is placed in a horizontal position.

10. The apparatus as recited in claim.1 where said specimen is placed in a horizontal position within an autoclave where conditions encountered in a deep well is simulated.

11. The apparatus as recited in claim 1 where said specimen is placed in a vertical position.

12. The apparatus as recited in claim 1 where said specimen is placed in a vertical position within an autoclave where conditions encountered in a deep well is simulated.

13. The apparatus as recited in claim 1 where said specimen is placed in a vertical position within an autoclave of substantially smaller diameter where conditions encountered in a deep well is simulated.

14. The apparatus as recited in claim 1 where said specimen is placed in a vertical position within an autoclave which has an inside diameter of about 4 to about 6 inches where conditions encountered in a deep well is simulated.

15. The method as recited in claim 1 where said applied force is dynamic.

16. A method for crack initiation and propagation within a metal under enclosed environmental conditions comprising:
    (a) supporting a metal specimen in said enclosed environment;
    (b) forming a specimen of a generally rectangular planar and cross sectional configuration having two longitudinal arms with a space therebetween for a substantially short distance terminating in oppositely disposed longitudinal grooves for the remainder of the distance therebetween which grooves define a narrowed longitudinal section;
    (c) applying a force, while said specimen is in said enclosed environment by a rod means interconnected to each of said arms in combination with said enclosed environment, sufficient to initiate and propagate a longitudinal crack in said longitudinal section; and
    (d) detecting strain via strain sensors and measuring said detection results from said crack initiation and propagation in said specimen which enables the prediction of the metal behavior under actual conditions of use.

17. The method as recited in claim 16 where said specimen is contained in a means for exposing said specimen to high prssures and high temperatures in combination with gases generally encountered in deep wells.

18. The method as recited in claim 16 where said specimen is contained within an autoclave where conditions encountered in deep wells are simulated.

19. The method as recited in claim 16 where in step (c) said rod means comprises two separate rods interconnected into holes in each of said arms which are thereafter connected to a gearing means and a load cell for monitoring the load applied to said arms.

20. The method recited in claim 16 where in step (c) said means for applying force comprises an enclosure around said specimen having at least two pins which pass through said enclosure and said specimen whereby said force is indirectly transferred to said specimen.

21. The method as recited in claim 16 where in step (d) said strain sensors comprise at least one pair of strain guages.

22. The method as recited in claim 16 where in step (d) said strain sensors comprise at least one pair of strain gauges.

23. The method as recited in claim 16 where in step (a) said specimen is a member selected from the group consisting of carbon steel, chromium alloys, corrosion resistant alloys, precipitation hardenable alloys, duplex alloys, austenitic stainless steel, nickel-based alloys, and cobalt-based alloys.

24. The method as recited in claim 16 where said specimen is placed in a horizontal position.

25. The method as recited in claim 16 where said specimen is placed in a horizontal position within an autoclave where conditions encountered in a deep well is simulated.

26. The method as recited in claim 16 where said specimen is placed in a vertical position.

27. The method as recited in claim 16 where said specimen is placed in a vertical position within an autoclave where conditions encountered in a deep well is simulated.

28. The method as recited in claim 16 where said specimen is placed in a vertically position within an autoclave of substantially smaller diameter where conditions encountered in a deep well is simulated.

29. The method as recited in claim 16 where said specimen is placed in a vertical position within an autoclave which has an inside diameter of about 4 to about 6 inches where conditions encountered in a deep well is simulated.

30. The method as recited in claim 16 where said applied force is dynamic.

31. A method for crack initiation and propagation within a metal under enclosed environmental conditions comprising:
(a) supporting a metal specimen in said enclosed environment;
(b) forming a specimen of a generally rectangular planar and cross sectional configuration having two longitudinal arms with a space therebetween for a substantially short distance terminating in oppositely disposed longitudinal grooves for the remainder of the distance therebetween which grooves define a narrowed longitudinal section;
(c) applying a force to each of said arms in combination with said enclosed environment, sufficient to initiate and propagate a longitudinal crack in said longitudinal section via a substantially mode one stress while said specimen is in said enclosed environment; and
(d) detecting strain via strain sensors and measuring said detection results from said crack initiation and propagation in said specimen which enables the prediction of the metal behavior under actual conditions of use.

32. The method as recited in claim 31 where said specimen is contained in a means for exposing said specimen to high pressures and high temperatures in combination with gases generally encountered in deep wells.

33. The method as recited in claim 31 where said specimen is contained within an autoclave where conditions encountered in deep wells are simulated.

34. The method as recited in claim 31 where in step c) said rod means comprises two separate rods interconnected into holes in each of said arms which are thereafter connected to a gearing means and a load cell for monitoring the load applied to said arms.

35. The method recited in claim 31 where in step (c) force is applied by an enclosure around said specimen having at least two pins which pass though said enclosure and said specimen whereby said force is indirectly transferred to said specimen.

36. The method as recited in claim 31 where in step (d) strain is detected by at least one pair of strain sensors.

37. The method as recited in claim 31 where in step (d) strain is detected by at least one pair of strain gauges.

38. The method as recited in claim 31 where in step (a) said specimen is a member selected from the group consisting of carbon steel, chromium alloys, corrosion resistant alloys, precipitation hardenable alloys, duplex alloys, austenitic stainless steel, nickel-based alloys, and cobalt-based alloys.

39. The method as recited in claim 31 where in step (c) force is applied by placing a solid wedge between said arms.

40. The method as recited in claim 31 where in step (c) force is applied by placing an expandable, substantially rectangular, wedge between said arms.

41. The method as recited in claim 31 where in step (c) force is applied by placing an expandable, substantially rectangular, wedge, with a means for controlling said force, between said arms.

42. The method as recited in claim 31 where in step (c) force is applied by connecting a rod means to each of said arms.

43. The method as recited in claim 31 where in step (c) force is applied indirectly by a means for holding said specimen.

44. The method as recited in claim 31 where in step (c) force is applied indirectly by a means for holding said specimen where said force is generated by an expandable, substantially rectangular, wedge means.

45. The method as recited in claim 31 where in step (c) force is applied indirectly by a means for holding said specimen where said force is generated by an expandable, substantially rectangular, wedge means combined with a means for controlling said force between said arms.

46. The method as recited in claim 31 where said specimen is placed in a horizontal position.

47. The method as recited in claim 31 where said specimen is placed in a horizontal position within an autoclave where conditions encountered in a deep well is simulated.

48. The method as recited in claim 31 where said specimen is placed in a vertical position.

49. The method as recited in claim 31 where said specimen is placed in a vertical position within an autoclave where conditions encountered in a deep well is simulated.

50. The method as recited in claim 31 where said specimen is placed in a vertical position within an autoclave of substantially smaller diameter where conditions encountered in a deep well is simulated.

51. The method as recited in claim 31 where said specimen is placed in a vertical position within an autoclave which has an inside diameter of about 4 to about 6 inches where conditions encountered in a deep well is simulated.

* * * * *